United States Patent [19]

Malmqvist et al.

[11] Patent Number: 5,762,675
[45] Date of Patent: Jun. 9, 1998

[54] METHOD RELATING TO THE PREPARATION OF AMORPHOUS SAMPLES AND MEANS THEREFOR

[75] Inventors: Johan Malmqvist; Ann-Christine Jacobsson; Rasema Kovacevic; Per-Erik Lindström, all of Skellefteå, Sweden

[73] Assignee: Boliden Minerals AB, Skelleftehamn, Sweden

[21] Appl. No.: 743,179

[22] Filed: Nov. 5, 1996

[51] Int. Cl.$^6$ .................................................. C03B 7/08
[52] U.S. Cl. .................. 65/66; 65/126; 65/325; 588/11; 588/17
[58] Field of Search ................... 65/66, 123, 126, 65/129, 134.8, 144, 324, 347, 374.13, 325; 588/11, 17; 73/864.91, 863.11, 863.31, 863.86

[56] References Cited

U.S. PATENT DOCUMENTS

| | | | |
|---|---|---|---|
| H480 | 6/1988 | Welch | 65/287 |
| 1,657,640 | 1/1928 | Peiler | 65/126 X |
| 2,201,049 | 5/1940 | Moore | 65/26 |
| 3,230,291 | 1/1966 | Walz | 373/28 |
| 3,853,525 | 12/1974 | Gorman | 65/181 |
| 4,045,202 | 8/1977 | Glaisse | 65/178 |
| 4,609,392 | 9/1986 | Claisse | 65/134.7 |
| 4,662,924 | 5/1987 | Kobayashi et al. | 65/66 |
| 4,793,844 | 12/1988 | Panayotov | 65/63 |
| 4,847,008 | 7/1989 | Boatner et al. | 588/11 |
| 5,266,094 | 11/1993 | Johansson et al. | 65/66 |
| 5,424,042 | 6/1995 | Mason et al. | 422/159 |

FOREIGN PATENT DOCUMENTS 1422449  1/1976  United Kingdom.

*Primary Examiner*—Donald E. Czaja
*Assistant Examiner*—Sean Vincent
*Attorney, Agent, or Firm*—Burns, Doane, Swecker & Mathis, L.L.P.

[57] ABSTRACT

A method of producing amorphous sample bodies that can be used for optical spectral analysis and X-ray spectral analysis, by batch-wise smelting in a crucible a mixture of analysis sample and a flux. The method is characterized by allowing a controlled flow of molten material to run out of the crucible and successively down onto a horizontal receiving surface and there form the sample bodies. The mixture is smelted suitably at a temperature of between 800° and 1300° C., preferably at about 1000° C., and is carried out in a crucible having a hole in the bottom thereof. A apparatus for producing such amorphous sample bodies is also disclosed. The apparatus includes a smelt crucible provided with an opening in its lower part and which is designed to be downwardly tapered at least inside in order to prevent the mixture from coming out, but to facilitate running of molten material through the opening. The apparatus will also preferably include a casting plate or a mould for casting sample bodies positioned horizontally beneath the crucible. The method and apparatus can be used in the production of sample bodies for the analysis of geological material, inorganic environment test material and sulfidic and/or oxidic products from ferrous and non-ferrous production processes.

18 Claims, 1 Drawing Sheet

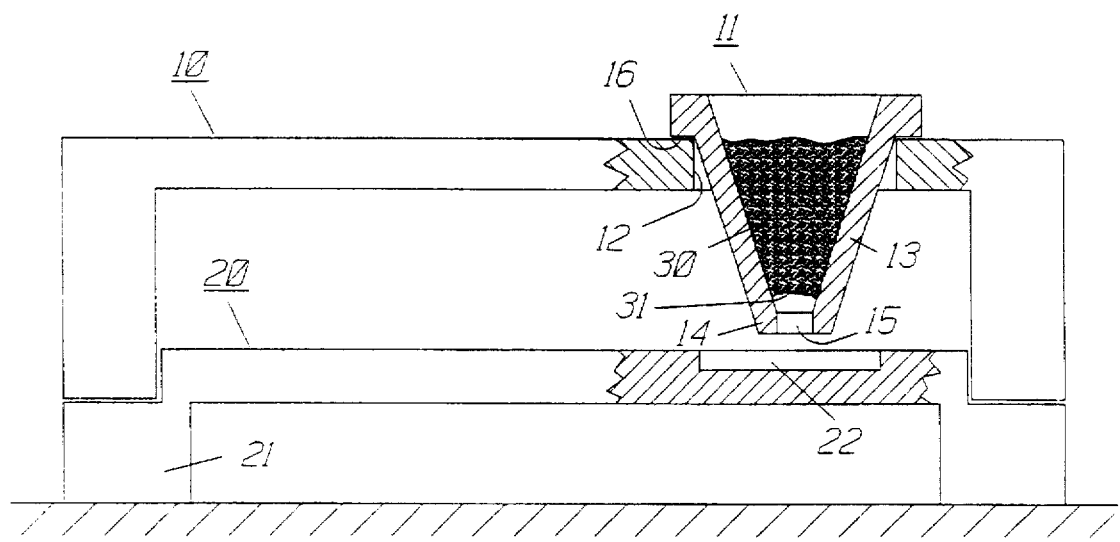

METHOD RELATING TO THE PREPARATION OF AMORPHOUS SAMPLES AND MEANS THEREFOR

BACKGROUND OF THE INVENTION

1. Field of the Invention

The present invention is concerned with a method relating to the preparation of amorphous sample bodies that can be used for optical spectral analysis and X-ray spectral analysis, by batch-wise melting in a crucible a mixture comprising an analysis sample and a flux. The invention also relates to means for preparing the sample and for practicing the method.

2. Description of the Related Art

A great deal of development work has been put into the preparation of sample bodies in recent decennia. This development work has been necessary because analysis sample bodies shall be as homogenous as possible in all types of analyses. A well-prepared amorphous glass has this property. In the case of X-ray spectral analysis for instance, it is difficult to work the sample mechanically (fine grinding or comminutiong) to achieve a homogeneity or particle grain size which will not have a disturbing affect on the subsequent analysis. In the case of optical spectral analysis, solutions that lack not-readily dissolved solids are normally required. Consequently, attempts have been made to develop more sophisticated smelting methods for the preparation of amorphous sample bodies. These smelting methods are generally based on mixing the analysis sample with a flux and thereafter melting the sample-flux mixture and moulding the smelt in an appropriate mould to obtain a glass briquette. Different borates are mainly used as the flux material, for instance lithium tetraborate, although the use of other flux materials is mentioned in the literature, such as lanthanum oxide, lithium metaborate, etc. The results obtained with this method of preparing sample bodies for optical and X-ray analysis are considered to be of such high quality that each sample material that will dissolve in a borate glass produced with the aforesaid conventional flux is now analyzed by spectral analysis. Difficulties are experienced in preparing homogenous sample bodies in the case of many materials, for instance materials which contain high concentrations of basic oxides, sulphides or which have high metal contents. In such cases, crystalline formations frequently occur which, in practice, make it impossible to analyze sample bodies of many different types of inorganic material, for instance geological samples, environmental samples, sulfidic and/or oxidic products that contain different intermediate products from ferrous and non-ferrous manufacturing processes.

Described in an article in X-ray Spectrometry, Vol. 19, pp. 3–14 (1990) is one of the latest proposed sample preparation methods for the analysis of geological samples, the so-called LDF method (Low Dilution Fusing). The method has been developed with the intention of solving sample preparation problems in respect of particularly troublesome rock species and minerals, for instance lamproites and kimberlites, these minerals having been formed under high pressures and temperatures. The flux used is a mixture comprising 20% lithium tetraborate and 80% lithium metaborate. An oxidation agent is also added, for instance one of the following: $NH_4NO_3$, $LiNO_3$, and $NaNO_3$. The oxidizable constituents are oxidized during smelting of the sample-flux mixture.

X-ray Spectrometry, Vol. 19, pp. 67–71 (1990) describes a smelting method used at Mount Isa Mines for many years in the preparation of geological sample bodies and different smelter products. A short pre-oxidation process with sodium nitrate at 70° C. has been included in this method to enable the preparation of sulphide-containing sample bodies. The additives used in other respects comprise a conventional flux consisting of different lithium borates.

Many of the materials relevant for analysis in laboratories that are associated with mines and smelting plants have such high sulphur and/or heavy metal concentrations as to necessitate their analyses by other methods, since it has not been possible to produce sample bodies of sufficient homogeneity hitherto. It can be mentioned by way of example that when testing the LDF method in the analytical laboratory at the Rönnskär smelting plant, sample bodies of different types of matte, white metal (i.e. concentrate matte) and oxide products of high zinc contents indicated several crystalline phases in the X-ray diffraction process.

Another method of preparing amorphous sample bodies, including sample bodies from the aforesaid problematic material, is described in Applicant's U.S. Pat. No. 5,266,094, which is incorporated in the present document by reference. As with the earlier known sample preparation methods, smelting is effected in a laboratory furnace in conventional platinum laboratory crucibles, which are removed from the furnace with the aid of crucible tongs after a given time has lapsed, and the smelt contained in the crucible is poured into a sample mould to form a sample body. This method of smelting and casting sample bodies thus requires the use of particularly expensive crucible material, as conventional laboratory crucibles are made of platinum. Each crucible can only be used for a limited number of analyses, partly because of the wear to which the crucibles are subjected during the smelting processes, and partly, and mainly, as a result of contamination by readily alloying elements, such as Co, Ni, Cu and noble or precious metals included in the sample, which naturally also jeopardizes subsequent analysis of these elements. Furthermore, the personnel preparing the sample must be very adroit when handling crucibles and crucible tongs, so as to ensure that nothing will be spilt from the crucible as it is placed into and removed from the furnace, and while moulding the sample bodies.

Consequently, there is a need to further develop sample preparation methods so as to enable amorphous, homogenous sample bodies to be prepared from all of the materials that can be made the subject of analysis in, e.g., the laboratory of a smelting plant. One reason in this respect is the need to keep analysis costs low, for instance by rationalizing sample preparation so that all materials to be analyzed can be prepared in one and the same way and preferably with solely one single sample preparation. Neither is it possible to lower the accuracy to which the analyses are carried out, and consequently particularly high and very specific requirements must be placed on the sample preparation method applied. It is therefore desirable that the preparation of amorphous sample bodies can be improved so as to enable cheaper materials to be used and so that manual handling in conjunction with the moulding of sample bodies can be made easier and more effective, but primarily so that analyses of elements that are able to alloy with platinum can be carried out with greater precision.

Accordingly, one object of the present invention is to provide a method in which the aforesaid drawbacks associated with the preparation of amorphous sample bodies are essentially fully eliminated. The invention is characterized to this end by the steps and features set forth below.

DESCRIPTION OF THE PREFERRED EMBODIMENTS

Smelting of the mixture containing an analysis sample and flux is carried out whilst casting sample bodies at the same time. As the mixture begins to melt, the molten material runs down in a controlled flow onto a horizontal underlying surface where the smelt is collected and permitted to solidify into solid, amorphous sample bodies. The smelting process is suitably effected in a crucible provided with a hole and constructed so that the mixture will not leave the crucible through the hole prior to melting, and so as to facilitate running of the smelt from the crucible. The flow of smelt running from the crucible is controlled by appropriately adapting the diameter of the hole.

Smelting is suitably carried out in a temperature range of 800°–1300° C., for instance at a temperature of about 1000° C., which has been found to provide amorphous sample bodies of sufficient homogeneity when sulphur-containing sample bodies are to be prepared, and which afford the requisite analysis accuracy.

The inventive arrangement for preparing amorphous sample bodies by batch-wise melting of a mixture of a sample intended for analysis and a flux includes a smelt crucible which is provided with an opening in its lower part and at least an inside that is designed to be tapering downwards in order to prevent the mixture from coming out, but to facilitate flowing of molten material through said opening. The crucibles may be modified smelt crucibles conventionally used for analysis purposes, for instance platinum crucibles, wherein the modification comprises a hole in the bottom of the crucible and optionally the use of an insert, for instance a ceramic insert, which facilitates running of the molten material from the crucible. The invention also enables special, non-conventional crucibles shapes to be used, for instance tapering or conical shapes. Thus, the method enables the use of platinum crucibles and the like, wherein the effective useful life of the crucibles is extended because the time in which the molten material is in contact with the metal wall of the crucible is shorter than in the case of conventional smelting processes. However, the aforementioned alloying problem still remains to a large extent, i.e. the take-up of certain metals in the crucibles, and consequently it is preferred to use instead smelt crucibles that are made of non-metallic materials. It has surprisingly been found that the novel method allows the use of non-metallic materials that have earlier been unusable, probably because it was not earlier possible to reduce the smelt-crucible contact time sufficiently to eliminate contamination. This contamination is caused partly by dissolution of the crucible material in the smelt and partly by smelt being alloyed in the crucible wall. The inventive method thus enables the use of much cheaper smelt crucibles than was earlier possible and also enables sample bodies to be prepared in the absence of any appreciable risk of any contamination that may cause wear on crucibles and also present analysis problems.

A suitable ceramic crucible material is boron nitride. The crucibles may be produced entirely from boron nitride, by pressing or pyrolytically, although it is also possible to use a less expensive ceramic material for the actual crucible and thereafter coat at least the internal surfaces of the crucible with boron nitride.

The sample bodies may be moulded or cast directly on an existing horizontal underlying surface over which the crucible has been placed, although it is preferred that the arrangement will also include a separate casting plate or mould placed horizontally beneath the crucible.

The plate or mould will preferably be placed at a distance of 1–20 mm from the exit orifice of the hole in the bottom of the crucible. The crucibles may advantageously be made of ceramic material, for instance refractory casting material of commercial quality, for instance from Höganäs or Silikaverken, both of which providing such qualities, which can withstand temperatures in excess of 1300° C. Graphite crucibles can also be used in some cases. The crucible may have different, downwardly narrowing shapes, at least internally, provided that the mixture will not leave the crucible through said opening prior to melting of the mixture. However, a conical crucible has been found to be best from both the aspect of manufacture and of use. There can be used a refractory crucible rack having room for several crucibles, with a casting plate provided with moulds beneath each crucible, so as to enable sample bodies to be prepared both quickly and effectively.

BRIEF DESCRIPTION OF THE DRAWING

The invention will now be described in more detail with reference to the accompanying drawing, the single FIGURE of which is a longitudinal, partially sectioned view of a preferred inventive arrangement, and with reference to an exemplifying series of analyses which illustrate the reliability of sample bodies prepared in accordance with the invention.

Shown in the FIGURE is a crucible rack 10 which accommodates sample smelt crucibles 11, of which only one is shown in the FIGURE. The rack includes a plurality of crucible receiving holes 12 whose sizes are adapted to chosen crucible sizes. Each crucible 11 has a conical, downwardly tapering part 13, and a bottom 14 in which an opening 15 is provided. The upper part of the crucible 11 has a horizontal rim or edge 16 adapted to the size of holes 12. A suitable crucible will have a height of about 45 mm, an outer diameter of the same size, and a hole diameter of about 4 mm.

The crucible rack 10 is placed on a mould rack 20 having legs 21 which rest on an existing horizontal supportive surface, for instance on the bottom of the furnace. The mould rack 20 has moulds 22 formed beneath each hole 12 in the crucible rack 10. The diameter and depth of respective moulds can be adapted to the nature of the sample bodies to be produced, but will suitably have a diameter of about 30–35 mm and a depth of about 5 mm.

Amorphous sample bodies are prepared in accordance with the invention by mixing a weighed sample quantity with flux. The mixture is transferred to a crucible 11 placed in the rack 10. Because of the conical configuration of the crucible 11 and the intrinsic internal friction of the fine-grain mixture, the sample mixture will form a bridge 31 at the bottom of the crucible. When all crucibles 11 in the rack 10 have been filled with respective sample mixtures 30, the crucible rack and the mould rack 20 are placed in a furnace chamber, with the crucible rack 10 placed over the mould rack 20 as shown in the FIGURE. When the mixture 30 begins to melt, molten material will run down in the crucible 11 and gradually melt the bridge 31 and therewith penetrate the bridge and pass out through the opening 15 and down into the mould 22. When all moulds 22 have been filled, the crucible rack 10, the mould rack 20 and the moulded sample bodies are allowed to cool. When these process stages have been completed, the used crucibles 11 and moulds 22 are removed from their respective racks 10 and 20 and replaced with fresh crucibles and moulds for continued sample preparation.

The invention will be described in more detail below in the form of examples which describe trials from assays and analyses carried out with XRF equipment of the Boliden laboratory with the aid of glass briquettes produced by the inventive method and with the inventive arrangement, the results of these trials being set forth in Table 1 and Table 2 below.

EXAMPLE 1

This example is intended to show the reproducibility of the method. A number of double sample-bodies were produced. The first pairs are five sediments of the twelve international Chinese GSD standards, and the remaining five are some of in-house standards, all of which have a highly complex nature and occur as reference samples in our activities. Table 1 discloses sample content and measured intensities of the double sample-bodies. The standard deviation has been calculated as the relative spread of measured intensities of respective double sample-bodies Std. Dev. $\underline{S}(\%) = \{\Sigma\{2(I_A - I_B)/(I_A + I_B)\}^2/(N-1)\}^{1/2} \times 100$, where $I_A$, $I_B$ = Measured intensities in counts/second (c/s) for the A and B sample respective. N = Number of pairs.

As a comparison, the statistical spread error in the mean value of the 20 intensity measurements was also calculated, as Sigma $\sigma(\%) = 1/(I)^{1/2} \times 100$

EXAMPLE 2

In this test series, the chosen sample was an arsenic concentrate having high concentrations of $SiO_2$, S, Fe and As, i.e. also volatile elements as S and As. Table 2 also discloses concentrations for the standard, ASS, concentrations calculated with an evaluation program (TNPP) for a number of different ASS sample bodies produced with the described apparatus and measured sample intensities. The first sample, ASSORG, was produced conventionally in platinum crucibles. The second sample, ASSPTI was prepared in a hot-pressed BN crucible (boron nitride) in accordance with the aforedescribed apparatus. The ASSPYK sample was produced in and with the aid of a pyrolytically produced BN cone, whereas the DGPT9A sample was oxidized and smelted in a BN-slurried ceramic crucible in accordance with the invention.

It will be seen from Table 1 that $\underline{S}$ is constantly smaller than or equally as large as $\sigma$ for elements whose atomic number is greater than that of potassium, with the exception of copper. This is because the copper channel has been attenuated and because the relative error will naturally increase in respect of sample bodies close to the detectable limit. $\underline{S}$ and $\sigma$ differ by a factor of ±3 in the case of the lightest elements Na to S, which is considered acceptable for these elements. A comparison is made in Table 2 between the ASS sample produced conventionally in the platinum crucible and the remaining sample bodies. Intensities and calculated concentrations are in good agreement, with the exception of the sample body produced in the BN-slurried crucible which has lost more sulphur than the remainder and which was shielded from BN powder entrained from the crucible walls. The sulphur yield is only about 85%, 85% and 65% respectively in the case of the ASS sample bodies produced in BN crucibles in comparison with the conventionally produced sample. The above Examples illustrate that the inventive. arrangement can be used to produce glass for sample bodies of varying composition and that this can be achieved with good reproducibility.

TABLE 1

Reproducibility test
Certified and recommended concentrations with assays of double samples for some International and Inhouse standards

| Sample | Na2O | MgO | Al2O3 | SiO2 | S | K2O | CaO | TiO2 | Cr | Mn | Fe2O3 | Co | Ni | Cu | Zn | As | Pb |
|---|---|---|---|---|---|---|---|---|---|---|---|---|---|---|---|---|---|
| GDS1 | 3.50 | 4.14 | 14.8 | 58.4 | 0.01 | 2.77 | 4.60 | 0.98 | 0.019 | 0.119 | 7.40 | 0.0023 | 0.0076 | 0.0022 | 0.0079 | 0.0002 | 0.0024 |
| GSD1A c/s | 179 | 543 | 11266 | 39819 | 246 | 1255 | 5034 | 1607 | 303 | 1180 | 13917 | 651 | 1020 | 240 | 220 | 5216 | 5686 |
| GSD1B c/s | 179 | 544 | 11272 | 39820 | 247 | 1257 | 5038 | 1603 | 303 | 1181 | 13924 | 645 | 1021 | 236 | 220 | 5215 | 5692 |
| GSD4 % | 0.30 | 1.04 | 15.67 | 52.5 | 0.04 | 2.23 | 7.52 | 0.89 | 0.008 | 0.106 | 5.90 | 0.0018 | 0.004 | 0.0037 | 0.0101 | 0.002 | 0.003 |
| GSD4A c/s | 38 | 159 | 12205 | 37770 | 328 | 1019 | 8452 | 1480 | 248 | 1071 | 11494 | 621 | 964 | 274 | 239 | 5364 | 5853 |
| GSD4B c/s | 39 | 158 | 12028 | 37181 | 320 | 1015 | 8339 | 1464 | 245 | 1060 | 11329 | 624 | 958 | 261 | 236 | 5375 | 5836 |
| GSD7 % | 1.21 | 3.06 | 13.44 | 64.6 | 0.02 | 3.55 | 1.66 | 0.75 | 0.012 | 0.089 | 6.50 | 0.0021 | 0.0053 | 0.0038 | 0.0238 | 0.0084 | 0.035 |
| GSD7A c/s | 79 | 405 | 10513 | 43320 | 301 | 1535 | 1825 | 1266 | 280 | 967 | 12901 | 654 | 1012 | 264 | 317 | 5618 | 7447 |
| GSD7B c/s | 77 | 399 | 10333 | 42849 | 298 | 1532 | 1793 | 1244 | 276 | 963 | 12628 | 647 | 1003 | 254 | 314 | 5591 | 7376 |
| GSD10 % | 0.04 | 0.12 | 2.84 | 88.9 | 0.01 | 0.13 | 0.70 | 0.21 | 0.014 | 0.13 | 3.90 | 0.0015 | 0.003 | 0.0023 | 0.0046 | 0.0025 | 0.0027 |
| GSD10A c/s | 28 | 40 | 2120 | 54530 | 243 | 68 | 750 | 382 | 287 | 1259 | 7622 | 613 | 1024 | 248 | 223 | 5947 | 6451 |
| GSD10B c/s | 30 | 41 | 2182 | 55956 | 239 | 71 | 771 | 392 | 293 | 1286 | 7815 | 618 | 1030 | 266 | 230 | 5971 | 6459 |
| GSD11 % | 0.46 | 0.62 | 10.37 | 76.3 | 0.02 | 3.28 | 0.47 | 0.35 | 0.004 | 0.322 | 4.40 | 0.0009 | 0.0014 | 0.0079 | 0.0373 | 0.0188 | 0.0636 |
| GSD11A c/s | 70 | 101 | 8017 | 49127 | 265 | 1365 | 529 | 619 | 238 | 2634 | 8642 | 599 | 969 | 268 | 399 | 6075 | 9036 |
| GSD11B c/s | 45 | 99 | 8177 | 49423 | 250 | 1385 | 532 | 626 | 235 | 2631 | 8657 | 602 | 965 | 280 | 401 | 6076 | 9043 |
| ASS % | 0.34 | 0.94 | 4.55 | 18.5 | 26.6 | 0.69 | 1.60 | 0.31 | 0.032 | 0.027 | 42.7 | 0.30 | 0.012 | 0.23 | 0.99 | 9.96 | 0.14 |
| ASSA c/s | 44 | 144 | 2001 | 18860 | 32303 | 186 | 898 | 320 | 257 | 494 | 44093 | 2452 | 915 | 600 | 2312 | 79982 | 6329 |
| ASSB c/s | 43 | 146 | 2076 | 18942 | 32472 | 187 | 898 | 325 | 257 | 494 | 44090 | 2431 | 911 | 597 | 2320 | 79852 | 6299 |
| ANKIE % | 0.48 | 1.19 | 1.22 | 3.90 | 7.70 | 0.21 | 1.18 | 0.06 | 0.282 | 0.259 | 23.4 | 0.028 | 0.078 | 12.8 | 20.8 | 3.50 | 7.86 |
| ANKIEA c/s | 163 | 137 | 723 | 14713 | 11734 | 71 | 773 | 122 | 1095 | 1431 | 26356 | 1062 | 1793 | 20369 | 44419 | 23130 | 83243 |
| ANKIEB c/s | 164 | 141 | 715 | 14848 | 11696 | 72 | 774 | 121 | 1100 | 1432 | 26407 | 1065 | 1798 | 20444 | 44636 | 23275 | 83594 |
| ANKIG % | 0.04 | 0.59 | 0.51 | 2.20 | 50.0 | 0.07 | 0.24 | 0.001 | 0.012 | 0.006 | 60.8 | 0.008 | 0.001 | 0.05 | 0.07 | 0.08 | 0.04 |
| ANKIGA c/s | 29 | 78 | 334 | 14622 | 56883 | 40 | 409 | 78 | 245 | 365 | 60172 | 1075 | 749 | 280 | 290 | 4648 | 4943 |
| ANKIGB c/s | 29 | 78 | 335 | 14662 | 55364 | 37 | 411 | 81 | 242 | 359 | 60105 | 1080 | 747 | 301 | 292 | 4657 | 4948 |
| ANKIR % | 0.16 | 0.97 | 0.86 | 5.02 | 23.5 | 0.18 | 0.46 | 0.070 | 0.013 | 0.017 | 43.9 | 0.025 | 0.015 | 25.9 | 2.36 | 0.20 | 1.93 |
| ANKIRA c/s | 48 | 101 | 469 | 14184 | 33838 | 65 | 319 | 128 | 240 | 1031 | 45359 | 1155 | 959 | 34215 | 4770 | 4548 | 25780 |
| ANKIRB c/s | 48 | 101 | 514 | 14437 | 33068 | 64 | 309 | 125 | 243 | 1015 | 45113 | 1148 | 949 | 33294 | 4774 | 4570 | 25700 |
| ANKIV % | 0.03 | 0.03 | 0.01 | 0.01 | 19.01 | 0.01 | 0.06 | 0.003 | 0.005 | 0.002 | 0.80 | 0.005 | 0.713 | 76.8 | 0.25 | 0.14 | 1.40 |
| ANKIVA c/s | 35 | 31 | 278 | 10996 | 24819 | 16 | 141 | 65 | 218 | 305 | 1209 | 630 | 9212 | 119707 | 893 | 3572 | 16370 |
| ANKIVB c/s | 34 | 31 | 126 | 11232 | 25139 | 17 | 53 | 60 | 223 | 305 | 1223 | 632 | 9234 | 119650 | 884 | 3550 | 16309 |
| Std. div. S % | 3.1 | 4.8 | 3.8 | 1.5 | 2.5 | 3.7 | 1.7 | 2.8 | 1.4 | 1.1 | 1.1 | 0.7 | 0.6 | 4.4 | 1.3 | 0.4 | 0.4 |
| Mean 1 c/s | 70 | 174 | 5293 | 29862 | 16016 | 563 | 2103 | 605 | 311 | 1073 | 23153 | 950 | 17602 | 5396 | 14412 | 17120 |
| Sigma σ % | 11.9 | 7.6 | 1.4 | 0.6 | 0.8 | 4.2 | 2.2 | 4.1 | 5.7 | 3.1 | 0.7 | 3.2 | 2.3 | 0.8 | 1.4 | 0.8 | 0.4 |

TABLE 2

Comparison of an As-concentrate sample prepared in a Pt-crucible with some sample prepared in several different BN-crucibles.

| Sample | Na2O | MgO | Al2O3 | SiO2 | S | K2O | CaO | TiO2 | Cr | Mn | Fe2O3 | Co | Ni | Cu | Zn | As | Pb |
|---|---|---|---|---|---|---|---|---|---|---|---|---|---|---|---|---|---|
| ASS (Rek.) % | 0.34 | 0.74 | 4.55 | 18.5 | 22.8 | 0.69 | 1.40 | 0.31 | 0.032 | 0.037 | 40.7 | 0.172 | 0.022 | 0.24 | 0.97 | 9.73 | 0.16 |
| ASSORG % | 0.37 | 0.71 | 4.34 | 18.7 | 22.5 | 0.67 | 1.31 | 0.28 | 0.023 | 0.042 | 40.7 | 0.162 | 0.026 | 0.23 | 1.01 | 9.66 | 0.15 |
| ASSPTI % | 0.36 | 0.64 | 4.35 | 18.9 | 21.5 | 0.65 | 1.30 | 0.27 | 0.021 | 0.042 | 39.5 | 0.156 | 0.025 | 0.24 | 0.98 | 9.31 | 0.15 |
| ASSPYK % | 0.41 | 0.68 | 4.27 | 19.2 | 22.0 | 0.64 | 1.27 | 0.27 | 0.020 | 0.041 | 39.2 | 0.154 | 0.023 | 0.23 | 0.95 | 9.10 | 0.14 |
| DGPT9A % | 0.32 | 0.60 | 3.60 | 17.5 | 15.9 | 0.57 | 1.09 | 0.25 | 0.022 | 0.035 | 37.1 | 0.149 | 0.025 | 0.21 | 0.94 | 8.77 | 0.14 |
| ASSORG c/s | 44 | 148 | 2056 | 19282 | 39481 | 187 | 883 | 319 | 259 | 483 | 43691 | 2428 | 903 | 562 | 2314 | 80000 | 6262 |
| ASSPTY c/s | 44 | 143 | 2093 | 19124 | 32826 | 188 | 904 | 328 | 256 | 491 | 44120 | 2434 | 903 | 596 | 2329 | 80015 | 6297 |
| ASSPYK c/s | 45 | 145 | 2056 | 19301 | 33476 | 184 | 885 | 320 | 253 | 484 | 43682 | 2401 | 886 | 575 | 2260 | 78480 | 6191 |
| DGPT9A c/s | 43 | 141 | 1785 | 18864 | 25214 | 176 | 811 | 326 | 269 | 473 | 44246 | 2468 | 926 | 573 | 2387 | 80371 | 6299 |

We claim:

1. A method of preparing an amorphous sample body that can be subjected to optical spectral analysis and X-ray spectral analysis comprising:

placing a mixture of an analysis sample and a flux in a crucible having a hole in the bottom thereof;

placing the entire crucible in a furnace; and conducting batchwise smelting whereby the mixture melts, flows through the hole at the bottom of the crucible and onto a horizontal receiving surface thereby forming said sample body.

2. A method according to claim 1, wherein the mixture is smelted at a temperature between 800 and 1300 C.

3. A method according to claim 1, wherein the mixture is smelted at a temperature of about 1000 C.

4. A method according to claim 1, wherein the hole has a diameter of about 4 mm.

5. A method according to claim 1, wherein the bottom of the crucible is at a distance of 1–20 mm from the horizontal surface.

6. A method according to claim 1, wherein the horizontal surface is a mold.

7. A method according to claim 1, wherein the crucible is composed of a ceramic or graphite material.

8. A method according to claim 1, wherein the crucible is composed of boron nitride.

9. A method according to claim 1, wherein the crucible is coated with boron nitride.

10. A method according to claim 1, wherein the analysis sample is a material selected from the group consisting of geological material, inorganic environmental test material, sulfidic products from ferrous production processes, sulfidic products from non-ferrous production processes, oxidic products from ferrous production processes and oxidic products from non-ferrous production processes.

11. An apparatus for preparing an amorphous sample body that can be subjected to optical spectral analysis and X-ray spectral analysis comprising:

a smelt crucible having a hole in the bottom thereof and a downwardly tapered portion adjacent the hole wherein the hole and the downwardly tapered portion are selected to prevent a mixture of an analysis sample and a flux from flowing through the hole, but permits flow upon melting of the mixture; and a horizontal receiving surface which receives the melted mixture and forms said sample body.

12. An apparatus according to claim 11, wherein the horizontal receiving surface comprises a casting plate or mould positioned horizontally beneath the crucible.

13. An apparatus according to claim 12, wherein the casting plate or mold is positioned 1–20 mm from the hole at the bottom of the crucible.

14. An apparatus according to claim 11, further comprising a crucible rack that supports the crucible.

15. An apparatus according to claim 11, further comprising a mold rack which supports the crucible rack.

16. An apparatus according to claim 11, wherein the crucible is composed of a ceramic or graphite material.

17. An apparatus according to claim 11, wherein the crucible is composed of boron nitride.

18. An apparatus according to claim 11, wherein the crucible is internally coated with boron nitride.

* * * * *

UNITED STATES PATENT AND TRADEMARK OFFICE
CERTIFICATE OF CORRECTION

PATENT NO. : 5,762,675

DATED: : June 9, 1998

INVENTOR(S) : Johan Malmqvist et al

It is certified that error appears in the above-identified patent and that said Letters Patent is hereby corrected as shown below:

TITLE PAGE:

Please insert the priority data as filed on March 3, 1998 as follows:

11/23/95    Sweden    9504180-2

Under the U.S. Patent Documents, please amend the spelling of the sixth inventor's name as follows:

4,045,202    8/1977    <u>C</u>laisse

Signed and Sealed this

Sixteenth Day of March, 1999

*Attest:*

Q. TODD DICKINSON

*Attesting Officer*    *Acting Commissioner of Patents and Trademarks*